(12) United States Patent
Jeevanandam et al.

(10) Patent No.: US 7,892,162 B1
(45) Date of Patent: Feb. 22, 2011

(54) ARTERIAL INTERFACE

(76) Inventors: Valluvan Jeevanandam, 5541 S. Woodlawn Ave., Chicago, IL (US) 60637-1620; Roger William Snyder, 2051 Belvedere Ct., New Braunfels, TX (US) 78130

( * ) Notice: Subject to any disclaimer, the term of this patent is extended or adjusted under 35 U.S.C. 154(b) by 0 days.

(21) Appl. No.: 12/604,228

(22) Filed: Oct. 22, 2009

(51) Int. Cl.
*A61M 1/12* (2006.01)
(52) U.S. Cl. ........................................... 600/18
(58) Field of Classification Search ............... 600/16, 600/17, 18
See application file for complete search history.

(56) References Cited

U.S. PATENT DOCUMENTS

| | | | |
|---|---|---|---|
| 4,540,404 A * | 9/1985 | Wolvek | 604/103.05 |
| 5,147,318 A | 9/1992 | Hohn | |
| 5,509,902 A | 4/1996 | Raulerson | |
| 5,820,542 A * | 10/1998 | Dobak et al. | 600/16 |
| 5,876,367 A | 3/1999 | Kaganov et al. | |
| 6,210,318 B1 * | 4/2001 | Lederman | 600/18 |
| 7,059,338 B1 * | 6/2006 | Kincaid et al. | 137/14 |
| 2003/0083539 A1 | 5/2003 | Leschinsky | |
| 2005/0192604 A1 | 9/2005 | Carson et al. | |

OTHER PUBLICATIONS

Bard Dynaflow Instructions for Use (Dec. 2007).

* cited by examiner

*Primary Examiner*—Niketa I Patel
*Assistant Examiner*—Alyssa M Alter
(74) *Attorney, Agent, or Firm*—Scott E. Kamholz; Peter K. Sollins; Foley Hoag LLP

(57) ABSTRACT

Devices and methods are disclosed for implanting, positioning, removing and replacing devices that penetrate an artery.

21 Claims, 2 Drawing Sheets

ARTERIAL INTERFACE

SUMMARY

Devices and methods are disclosed for implanting, positioning, removing and replacing devices that penetrate an artery.

BACKGROUND

The use of intraaortic balloon pumps is a well known method for treating heart failure. The balloon pump is positioned inside the aorta, typically in the proximal descending aorta. The balloon pump (typically 40-50 milliliters in capacity) is inflated and deflated in time with the contraction of the left ventricle. During diastole, the balloon is inflated, thereby driving blood in the ascending aorta and aortic arch into the coronary arteries to supply oxygen to the heart muscle. During systole, as the left ventricle contracts, the balloon is deflated so as not to increase the afterload. This procedure is termed "counterpulsation."

Such balloon pumps are commonly placed in the body by attaching a vascular graft to an artery, advancing the balloon and its inflation catheter through the graft lumen until the balloon is dangling in the descending aorta, and then tying a suture around the graft in order to seal the graft around the inflation catheter and also to anchor the pump relative to the artery. This constitutes open surgery—a major operation.

DETAILED DESCRIPTION

One problem in using existing intraaortic balloon pumps as long-term devices is that parts can wear out, cause infections, or otherwise need to be replaced. After the graft is attached at the incision in the artery and thereby exposed to the bloodstream, the healing process causes clotted blood, granulation tissue and other material to accumulate around the incision and in the graft. Such tissue completely fills the available volume inside the graft except for the space occupied by the inflation catheter. Such tissue becomes a cohesive, sometimes solid, mass with the graft. Because the balloon, even in its deflated state, is much larger than the inflation catheter (the catheter being small to avoid occupying too much cross-section of the vasculature through which it runs), it is practically impossible to remove the balloon through the clogged graft or to thread a new balloon through. The current solution to this problem is to replace the entire graft every time the balloon is replaced, which requires repeating the highly invasive vascular grafting procedure from the beginning.

The focus, then, has been on avoiding failures that necessitate the costly and dangerous replacement surgeries. For example, extreme care is taken to avoid introducing infections, despite inconvenience and discomfort to the patient. Also, the pumps are made of especially durable materials that are resistant to normal body stresses, even at the expense of more desirable functional characteristics.

But the inventors realized that failures are inevitable; practically no implantable device can forever survive the stresses placed upon it by the living body. Living tissue is constantly repaired and maintained by normal body processes, while implanted devices tend to be attacked, compartmentalized, or otherwise isolated. At the very least, they do not benefit from normal repair and maintenance processes to help them resist normal stresses.

So the inventors hit upon an entirely new strategy: rather than continue dogged efforts at finding ways to prevent failures, they accepted that failures cannot be avoided and instead sought ways to make the replacement procedure faster, simpler, and safer. The disclosed systems and methods for interfacing the intraaortic balloon pump with the vasculature resulted from this strategy.

The vascular interface incorporates a "stopper" to fill the space between the graft and the inflation catheter. Because this space is filled from the beginning, body processes cannot invade the graft to fill that space with clotted blood, etc. (although there may be some minimal invasion around the stopper itself). As a result, when the time to replace the pump inevitably comes, the stopper can be slipped out of the graft, leaving a largely patent graft lumen. The graft lumen is wide enough to permit removal and replacement of the pump. The graft itself need not be removed and replaced, so the dangerous and time-consuming step of vascular surgery is avoided.

Figure 1:
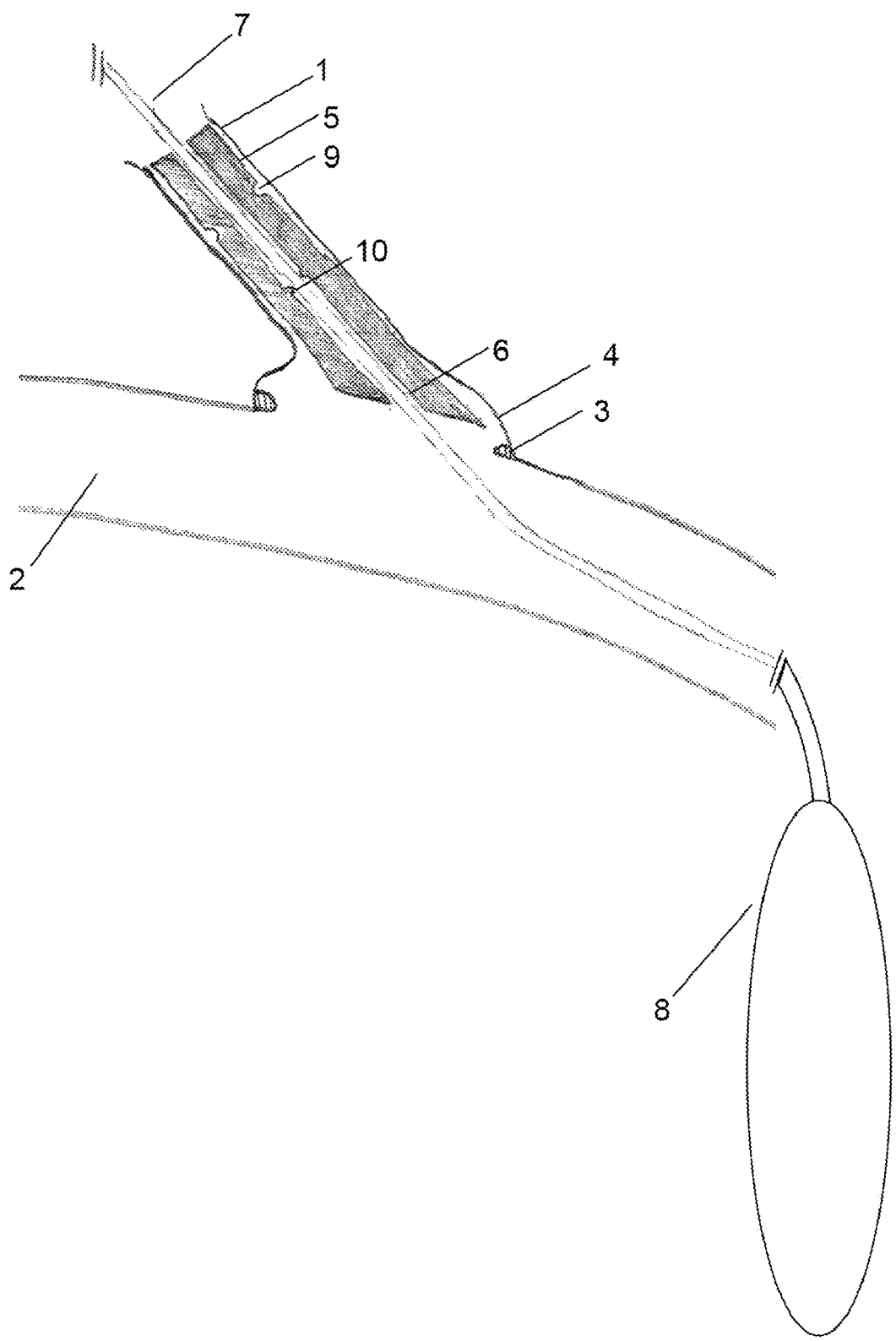
FIG. 1 schematically shows an intraaortic balloon pump implanted in a patient using an arterial interface.

FIG. 1 schematically shows an example of such a device, as deployed in a patient's vasculature. A vascular graft 1 is attached to an artery 2 with a suture ring 3 at the position of an incision in the artery. The particular graft shown flares at its distal end 4. The stopper 5 sits inside the graft 1, filling the interior of the graft 1 except for a hole 6 along the length of the stopper 5. The hole 6 necessarily runs the entire length of the stopper 5, but the stopper 5 need not run the entire length of the graft 1. It is sufficient that some part of the stopper 5 is near the distal end of the graft 4 when properly positioned. In some cases, the stopper can extend out past the proximal end of the graft, to help minimize clot invasion.

The hole 6 through the length of the stopper 5 is filled by the inflation catheter 7. The inflation catheter 7 in turn is connected at its distal end to a balloon or inflatable chamber 8. A typical inflation catheter will have a diameter in the range 3 to 6 mm (often about 5 mm), although other diameters are possible as well. In preferred embodiments, the catheter will be (i) wide enough inside to lower resistance to fluid flow to the point that air can be used as the pressure medium, with a pressure source that need generate no more than 0.5 atmospheres in order to transmit pressure from the source to the balloon chamber, and (ii) narrow enough outside so that the presence of the inflation catheter in the various blood vessels does not significantly interfere with the flow of blood through the vessels. In this context, "narrow enough to avoid significant interference" means that the catheter occludes less than 50% of the vessel's lumen.

Each component may be constructed of any of a variety of well-known biocompatible materials, such as polytetrafluoroethylene (PTFE), expanded PTFE (ePTFE), Dacron, polyurethane, polyethylene, silicone, and titanium. The inflation catheter 7 and/or balloon 8 in particular may also beneficially comprise a moisture resistant material to help prevent water from blood passing through the balloon wall and building up in the chamber. For example, moisture resistance may be achieved by laminating a moisture resistant material onto or into the inflation catheter 7 and/or balloon 8, or by applying moisture-resistant coating to the inner or outer surface of the balloon wall.

The stopper 5 may be useful in other ways besides preventing the build-up of tissue inside the graft 1. The stopper 5 can act as a cushion surrounding the inflation catheter 7 so as to help maintain the inflation catheter's patency when the graft is tied down. Also, the increased surface area of the stopper 5 as compared to the inflation catheter 7 can ease the task of sealing the graft 1.

Not shown in FIG. 1 is the proximal end of the inflation catheter 7. Because the balloon 8 needs to inflate and deflate in order to function as a ventricular assist device, the balloon pump must be in fluid communication with some sort of driver (e.g. an air compressor or pump) via the inflation catheter. If such a driver is to reside outside the body (as is typically done), a skin interface may be implanted. The skin interface, among other things, can help to decouple the internal parts of the pump assembly from the external parts. The inflation catheter can be attached to the interface, and the interface attached to the fluid driver. In this way, the driver, the inflation catheter 7 and the balloon 8 may form a closed air system; a closed system may include a well-defined and precisely-controlled volume of air, which facilitates leak detection. Air volume and movement of air may be precisely controlled using, for example, a bellows driven by one or more linear actuators.

The arterial interface device of FIG. 1 can be implanted in the body in a manner similar to the traditional intraaortic balloon pump described above. The graft 1 is attached to an artery 2 at an incision as described above. In addition to threading the balloon 8 and inflation catheter 7 through the graft 1, the stopper 5 is positioned in the graft 1, surrounding the inflation catheter 7. The balloon 8 is positioned in the descending aorta and, if the stopper 5 is a separate piece from the inflation catheter 7, the stopper 5 is positioned along the inflation catheter 7 so as to fill the distal end of the graft 1, near where the graft 1 is attached to the artery 2. The stopper 5 can be secured to the inflation catheter 7, and graft 1 is secured to the stopper 5.

To remove the balloon 8, one simply detaches the stopper 5 from the graft 1. Because the stopper 5 has prevented clots and other healing tissues from accumulating inside the graft 1, the stopper 5 can be removed easily, leaving the graft 1 unblocked. The balloon pump can then be removed by pulling the inflation catheter 7 and balloon 8 through the graft 1 lumen. A new balloon pump can be advanced through the open graft 1 lumen along with a new stopper 5. In this way, the balloon pump can be replaced without having to remove and replace the graft 1. Because the vascular graft 1 is left intact and relatively undisturbed, no open surgery is necessary to replace a damaged or worn out part. Such a procedure is relatively non-invasive and can be carried out in a catheterization laboratory rather than an operating room.

Figure 2:
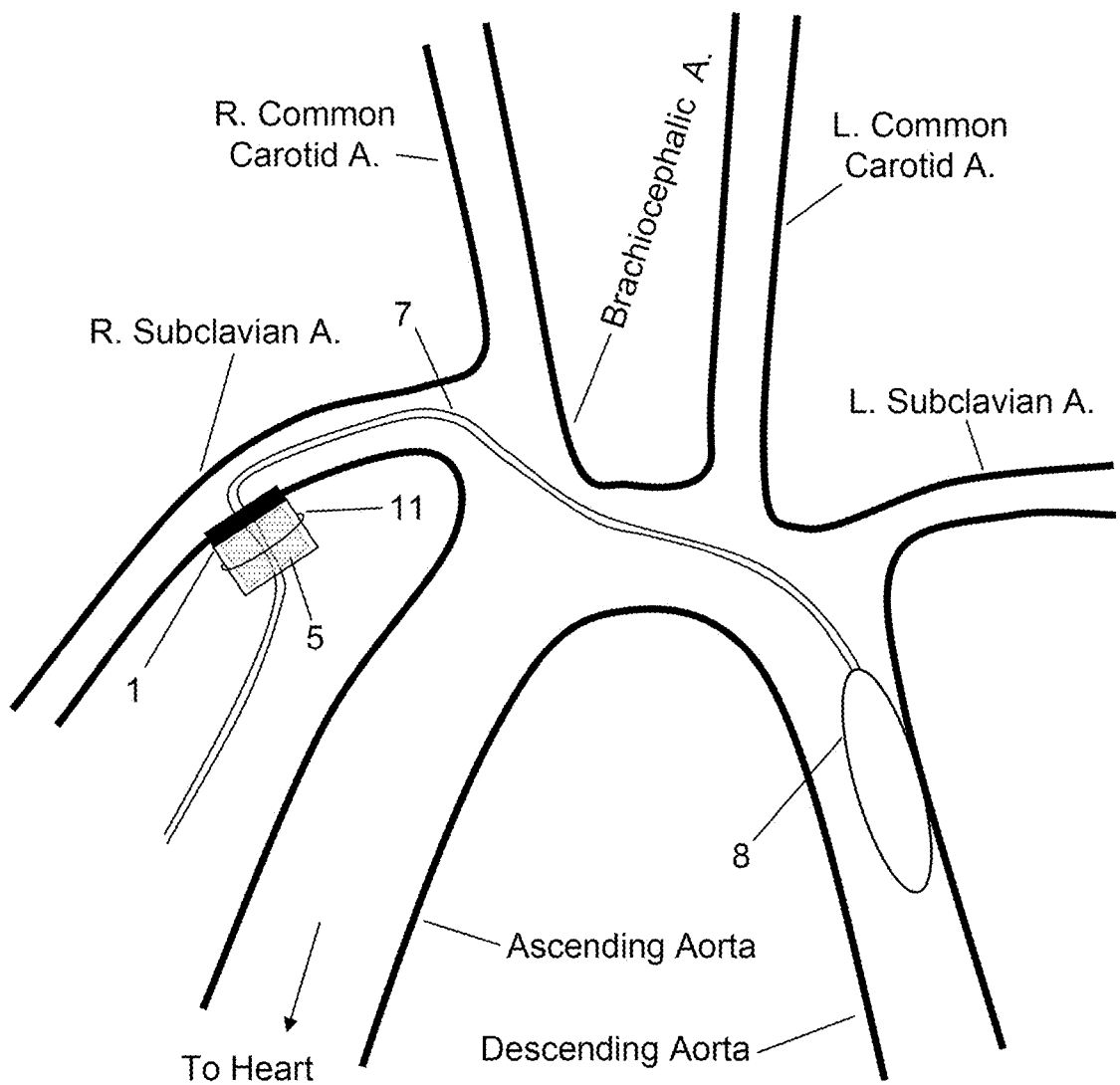
FIG. 2 schematically shows an intraaortic balloon pump positioned in the proximal descending aorta, with the pump's inflation catheter entering the vasculature at the right subclavian artery through an arterial interface.

One of skill in the art will appreciate that many configurations of the stopper 5 are possible. The stopper 5 could be sized to completely fill the graft 1 surrounding the inflation catheter 7, fitting snugly within the graft 1, or the stopper 5 could be smaller than the interior of the graft 1 so that, for example, the graft 1 is cinched down onto the stopper 5 with a suture or tie. (Suture or tie 11 is shown in FIG. 2). The stopper 5 could be integrally formed with the inflation catheter 7. The stopper 5 could have constant cross-sectional geometry, e.g., as a cylinder or prism, or the stopper 5 could be tapered or flared. The stopper 5 could be shaped to fit the interior of the particular vascular graft 1 being used. The stopper 5 could be made of two distinct pieces that form the entire stopper 5 when clamped together around the inflation catheter 7. The stopper 5 could be shaped with a circumferential notch 9 around its exterior to provide a convenient groove in which to run a tie or suture when securing the graft 1 to the stopper 5. The stopper 5 could also include a circumferential ridge 10 around the interior surface that defines the hole 6, the ridge 10 acting as a seal between the stopper 5 and the inflation catheter 7.

The hole 6 in the stopper 5 should be large enough to accommodate the inflation catheter 7, but too narrow to pass the balloon 8. Some outer dimension of the stopper 5 should be almost as large as, as large as, or larger than an outer dimension of the balloon 8 so that the balloon 8 can pass through the opening left after the stopper 5 has been removed without undue squeezing or compression. When in place, the stopper 5 should substantially fill the graft apart from the hole 6 for the inflation catheter. The hole 6 can account for various fractions of the smallest cross-sectional area of the stopper 5 including 75%, 60%, one half, one third, one quarter, or less.

FIG. 2 shows (schematically) the vascular interface is position on the right subclavian artery. This position is advantageous because it allows easy surgical access and a relatively short distance to the descending aorta. FIG. 2 also shows the graft secured to the stopper by a suture 11. Other suitable positions for the interface include either common carotid artery, the brachiocephalic artery, the left subclavian artery, the descending aorta, and the abdominal aorta. Downstream branches of the aorta may also be used, such as the external iliac and femoral arteries.

In addition to the components shown in FIGS. 1 and 2, it may be beneficial for the device to include various sensors. Sensors located at or near the balloon chamber will typically be connected to an electrical wire that, like the inflation catheter, passes through the stopper 5 and graft 1. The wire serves to pass the collected data out of the body, for instance to the fluid driver or an associated processor. Sensors that wirelessly transmit collected data are possible as well. Examples of sensors are electrical leads to measure the electrocardiogram, and sensors that detect pressure directly or indirectly. A wide variety of direct pressure sensors are known; the chamber itself can act as a pressure sensor when partially inflated. Indirect sensors include, for example, a microphone to monitor heart sounds. Data from these sensors can be used to monitor the cardiac cycle and, thereby, the counterpulsation cycle.

Sensors can also be used to determine the state of the air inside the system. Air pressure sensors can be used to detect whether the balloon pump is properly inflating, or if there is a leak in the system. A humidity sensor could be used to detect whether moisture has built up inside the balloon pump. The humidity sensor may be linked to a de-humidifier so that a certain level of humidity is not exceeded inside the balloon pump.

Although the drawings are directed to an intraaortic balloon pump, other indwelling arterial devices may be positioned using the disclosed arterial interface, such as indwelling arterial catheters ("A-lines"), dialysis lines, blood pumps such as axial flow pumps which add energy to flowing blood, and blood circulators such as those that remove blood from the aorta during systole and return it during diastole. While devices having distal ends larger than the catheters from which they extend may especially benefit, any device that may require replacement may benefit, as the stopper provides a convenient way to restore patency of the vascular graft for insertion of the replacement device.

We claim:

1. An intraaortic balloon pump assembly comprising an intraaortic balloon pump, a vascular graft, and a stopper, wherein:

the intraaortic balloon pump comprises an inflatable distal chamber and an elongate proximal inflation tube defining a channel in fluid communication with the chamber;

the vascular graft defines a graft lumen and comprises a distal end so sized and shaped as to be suited for grafting to an artery;

the stopper fills the graft lumen except for a hole defined through the stopper's length, the hole providing a conduit through the graft lumen;

the stopper comprises an exterior surface that defines one or more notches that receive ties placed around the vascular graft to secure the graft to the stopper;

the inflation tube passes through the conduit and is immobilized relative to the stopper;

the graft lumen is wide enough to allow passage of the balloon pump chamber; and the conduit is too narrow to allow passage of the balloon pump chamber.

2. The assembly of claim 1 further comprising a skin interface for attachment to an external driver, wherein the inflation tube has a proximal end coupled to the skin interface and a distal end coupled to the balloon pump chamber.

3. The assembly of claim 2 further comprising an external driver in fluid communication with the inflation tube channel, wherein the driver drives air in and out of the balloon pump distal chamber to inflate and deflate the chamber.

4. The assembly of claim 3 wherein the driver, the inflation tube channel and the balloon pump chamber define a closed air system.

5. The assembly of claim 4 wherein the balloon pump chamber is defined by a wall having a laminar structure, and wherein one layer of the laminar structure is moisture impermeable.

6. The assembly of claim 3 wherein the driver comprises a leak detection system.

7. The assembly of claim 3 wherein the driver comprises a dehumidifier.

8. The assembly of claim 3 wherein the driver comprises a bellows actuated by a linear actuator.

9. The assembly of claim 1 wherein the inflation tube is small enough to run inside a human aorta or an arch artery without occluding the aorta or artery.

10. The assembly of claim 1 wherein the stopper and the graft lumen are so sized and shaped that the stopper fits snugly within the graft lumen.

11. The assembly of claim 1 wherein the hole takes up no more than 60% of the stopper's smallest cross-sectional area measured transverse to the stopper's length.

12. The assembly of claim 1 wherein the hole takes up less than half of the stopper's smallest cross-sectional area measured transverse to the stopper's length.

13. The assembly of claim 1 wherein the hole takes up less than one third of the stopper's smallest cross-sectional area measured transverse to the stopper's length.

14. The assembly of claim 1 wherein the hole takes up about one quarter of the stopper's smallest cross-sectional area measured transverse to the stopper's length.

15. The assembly of claim 1 wherein the inflation tube has a diameter no more than 6 millimeters and no less than 3 millimeters.

16. The assembly of claim 1 wherein the stopper is formed as two pieces that are clamped into contact with one another around the inflation tube to immobilize the inflation tube relative to the stopper.

17. The assembly of claim 1 wherein the stopper is integrally formed with the inflation tube.

18. The assembly of claim 1 further comprising an electrically conductive wire passing through the conduit, the wire (a) connected to sensors located at or near the distal chamber and (b) conveying sensor signals to a processor.

19. A method of implanting the intraaortic balloon pump assembly of claim 1 into a subject, comprising:

incising an artery of the subject, the artery being the subject's aorta or one of the subject's arch arteries;

grafting the distal end of the vascular graft to the artery at the incision;

advancing the intraaortic balloon pump through the vascular graft, into the artery, and to a position at which the pump's distal chamber is positioned in the subject's descending aorta and a portion of the inflation tube extends through the graft;

positioning the stopper so that it fills the vascular graft lumen and surrounds the portion of the inflation tube that extends through the graft; and immobilizing the stopper relative to the vascular graft.

20. The method of claim 19, further comprising immobilizing the stopper relative to the intraaortic balloon pump.

21. An intraaortic balloon pump assembly comprising an intraaortic balloon pump, a vascular graft, and a stopper, wherein:

the intraaortic balloon pump comprises an inflatable distal chamber and an elongate proximal inflation tube defining a channel in fluid communication with the chamber;

the vascular graft defines a graft lumen and comprises a distal end so sized and shaped as to be suited for grafting to an artery;

the stopper fills the graft lumen except for a hole defined through the stopper's length, the hole providing a conduit through the graft lumen;

the inflation tube passes through the conduit and is immobilized relative to the stopper;

a stopper interior surface defines the hole, and the stopper interior surface comprises a raised ridge that provides a surface against which the inflation tube may be immobilized within the stopper;

the graft lumen is wide enough to allow passage of the balloon pump chamber; and the conduit is too narrow to allow passage of the balloon pump chamber.

* * * * *